United States Patent
Holtman et al.

(10) Patent No.: US 8,710,070 B2
(45) Date of Patent: Apr. 29, 2014

(54) OPIOID-KETAMINE AND NORKETAMINE CODRUG COMBINATIONS FOR PAIN MANAGEMENT

(75) Inventors: Joseph R. Holtman, Lexington, KY (US); Peter A. Crooks, Nicholasville, KY (US); Ujjwal Chakraborty, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 397 days.

(21) Appl. No.: 12/934,946

(22) PCT Filed: Mar. 27, 2009

(86) PCT No.: PCT/US2009/038651
§ 371 (c)(1),
(2), (4) Date: Jan. 20, 2011

(87) PCT Pub. No.: WO2009/131794
PCT Pub. Date: Oct. 29, 2009

(65) Prior Publication Data
US 2011/0112131 A1    May 12, 2011

Related U.S. Application Data

(60) Provisional application No. 61/072,090, filed on Mar. 27, 2008.

(51) Int. Cl.
*A61K 31/44* (2006.01)
*A61K 31/35* (2006.01)
*C07D 405/00* (2006.01)
*C07D 221/22* (2006.01)

(52) U.S. Cl.
USPC ............. 514/282; 514/454; 546/207; 546/44

(58) Field of Classification Search
USPC ................... 546/207, 282, 44; 514/282, 454
See application file for complete search history.

(56) References Cited

U.S. PATENT DOCUMENTS

| | | | |
|---|---|---|---|
| 5,460,826 A | 10/1995 | Merrill et al. | |
| 5,952,499 A | 9/1999 | Whittaker et al. | |
| 6,713,470 B2 * | 3/2004 | Jackson | 514/211.05 |
| 6,855,807 B1 * | 2/2005 | Devi et al. | 530/350 |
| 2004/0092531 A1 | 5/2004 | Chizh et al. | |
| 2004/0248964 A1 | 12/2004 | Crooks et al. | |
| 2007/0123468 A1 | 5/2007 | Jenkins et al. | |

OTHER PUBLICATIONS

International Search Report dated Sep. 4, 2009 (One (1) page).

* cited by examiner

*Primary Examiner* — Andrew D Kosar
*Assistant Examiner* — Raymond Covington
(74) *Attorney, Agent, or Firm* — Crowell & Moring LLP

(57) ABSTRACT

The present invention relates to the field of pain management, and more particularly to synergistic codrugs comprising an opioid and ketamine or norketamine which have been combined to form a single chemical codrug entity. When the codrug is administered it produces a synergistic analgesic response to pain.

47 Claims, 7 Drawing Sheets

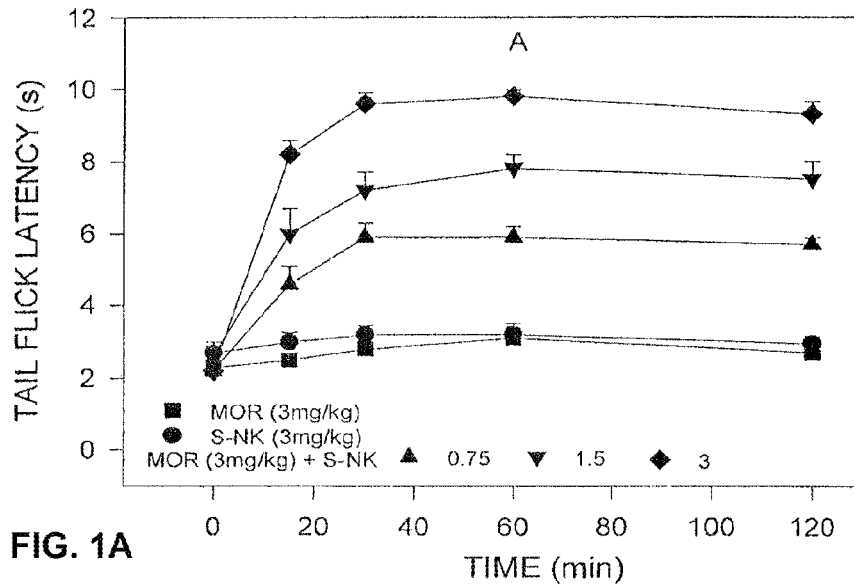
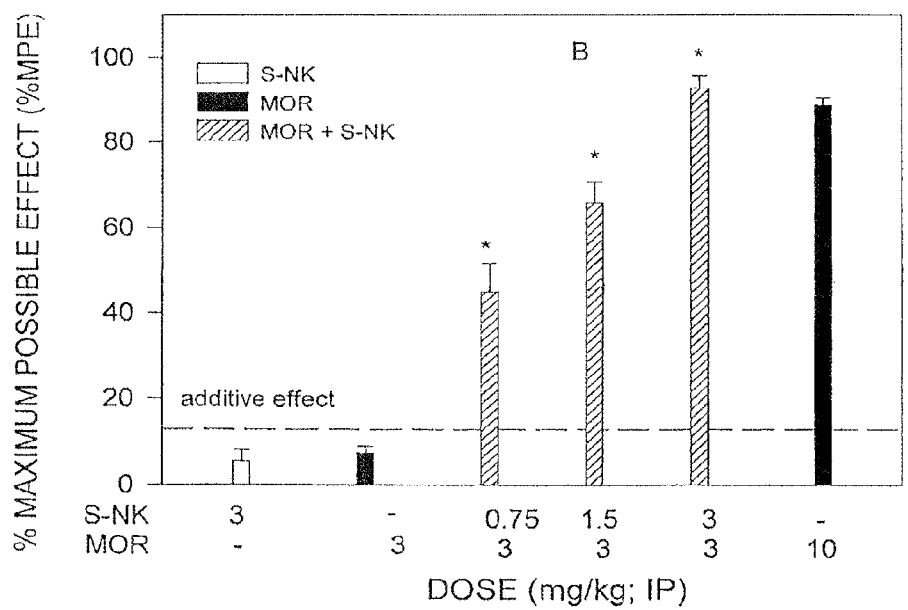

Mean +/- SEM (n = 7-9 rats); * Different from MOR (0.5 mcg) alone (P<0.05; post-hoc SNK)

OPIOID-KETAMINE AND NORKETAMINE CODRUG COMBINATIONS FOR PAIN MANAGEMENT

This application claims priority from U.S. Provisional Patent Application No. 61/072,090, filed Mar. 27, 2008, the disclosure of which is hereby incorporated by reference in its entirety.

FIELD OF THE INVENTION

The present invention relates to the field of pain management, and more particularly to synergistic codrugs comprising an opioid and ketamine or norketamine which have been combined to form a single chemical codrug entity. When the codrug is administered it produces a synergistic analgesic response to pain.

BACKGROUND OF INVENTION

Opioids are any endogenous or exogenous compounds that bind to an opioid receptor. Opioid receptors are localized primarily in the brain, spinal cord, and gastrointestinal tract. There are four broad groups of opioids: endogenous opioid peptides produced in the body; naturally occurring opioid alkaloids such as morphine and codeine; semisynthetic opioids such as hydrocodone and oxycodone, and synthetic opioids such as fentanyl and methadone. When opioids bind to their receptors in the brain and spinal cord they block pain transmission signals from the periphery of the body. Although opioids are very effective for moderate to severe pain, there are many well known problems associated with opioid therapy. Those problems include serious side effects such as cognitive dysfunction, respiratory depression, nausea/vomiting, urinary retention, and constipation. Further, chronic opioid therapy often results in the development of tolerance to the analgesic effect (resulting in dose escalation) as well as physical and psychological dependence.

N-methyl-D-aspartate antagonists are known to be effective in suppressing the symptoms of opiate withdrawal. The anesthetic ketamine is the most potent N-methyl-D-aspartate antagonist available in clinical practice. See, for example, WO/2004/045601.

There is a great need for analgesic medications able to provide high efficacy pain relief while providing more favorable pharmacokinetics and reducing the possibility of undesirable effects. Therefore, there is a need for a way to administer opioids and norketamine to provide a more favorable and pharmacokinetic profile.

SUMMARY OF THE INVENTION

In one embodiment, the present invention provides a codrug of the following formula:

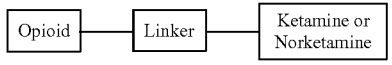

As well as compositions comprising same. The linker may be

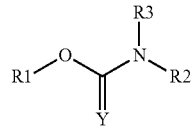

wherein Y is O or S; and R1-O is an opioid moiety and R2-N—R3 is a norketamine (R3=H) or ketamine (R3=CH$_3$) moiety; or

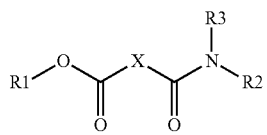

wherein X is nothing, O, S, NH, NR4 (R4=alkyl), (CH$_2$)$_x$ (where x=1-20, and the alkane moiety can be linear or branched), and wherein R2-N—R3 is a norketamine moiety (R3=H) or a ketamine moiety (R3=CH$_3$), and R1-O is an opioid moiety.

In another embodiment, the present invention provides a method of synthesis of a codrug comprising a linker, an opioid and a ketamine or a norketamine, said method comprising: a) covalently bonding a first attachment point of the linker to the opioid; b) covalently bonding a second attachment point of the linker to the ketamine or norketamine; and c) recovering the codrug, wherein the norketamine is selected from the group consisting of S-norketamine, R-norketamine, and racemic norketamine; and wherein the ketamine is selected from the group consisting of S-ketamine, R-ketamine, and racemic ketamine.

In a further embodiment, the present invention provides a method of treatment comprising joining an opioid together with a ketamine or a norketamine using a linker to form a cleavable codrug; and administering an analgesically effective amount of the codrug to a human patient, wherein the norketamine is selected from the group consisting of S-norketamine, R-norketamine, and racemic norketamine and wherein the ketamine is selected from the group consisting of R-ketamine, S-ketamine and racemic ketamine.

BRIEF DESCRIPTION OF THE DRAWINGS

FIG. 1 is a graph illustrating the effect of S-norketamine and morphine (MOR) combinations, using the tail flick test, via intraperitoneal administration. FIG. 1A shows tail flick latencies, and FIG. 1B shows the maximum possible effect.

FIG. 2 is a graph illustrating the effect of S-norketamine and morphine (MOR) via the tail flick test, using intrathecal administration.

FIG. 3 is a graph illustrating the effect of morphine (MOR) with S-Norketamine (S-NK) using chronic constriction nerve injury assay and intraperitoneal administration.

FIG. 4 is a graph illustrating the effect of morphine (MOR) with S-Norketamine (S-NK) using chronic constriction nerve injury assay and intraperitoneal administration.

DETAILED DESCRIPTION

Figure 2A:
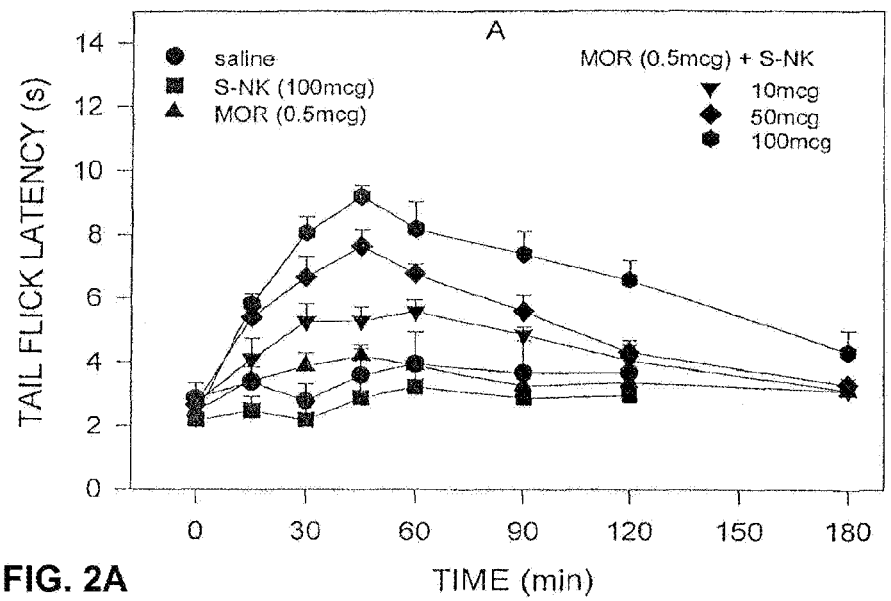
FIG. 2A shows tail flick latencies.
Figure 2B:
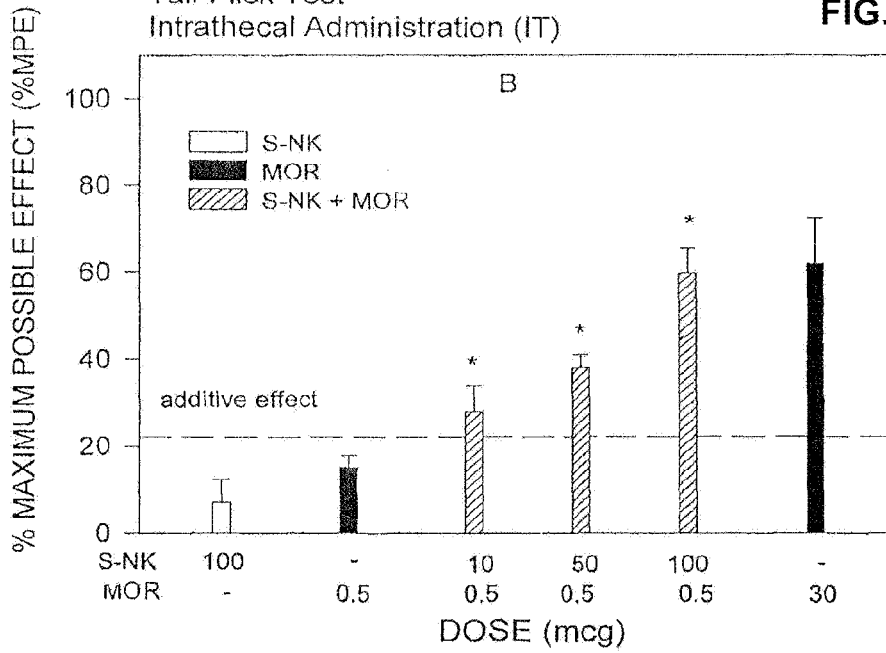
FIG. 2B shows the maximum possible effect.
Figure 3A:
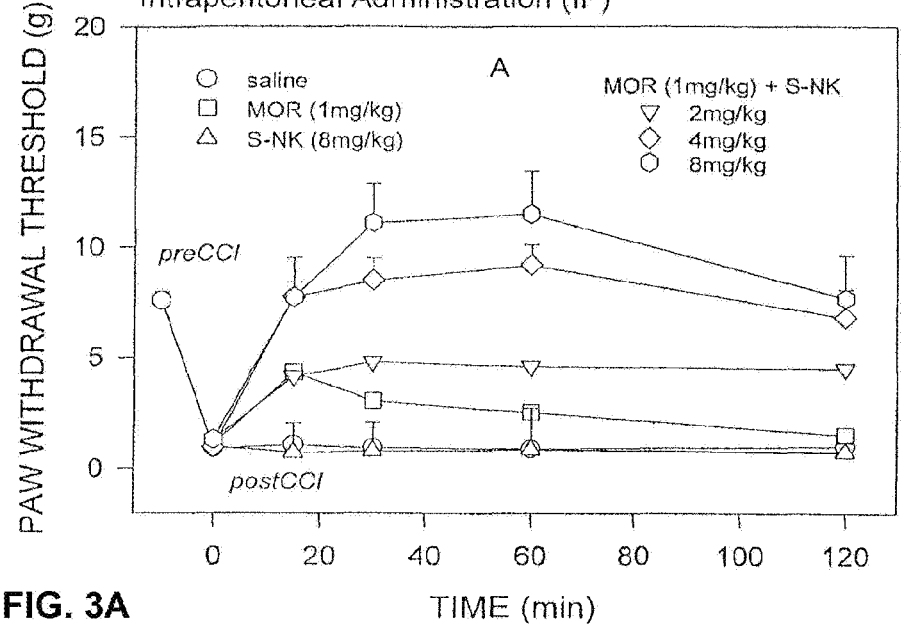
FIG. 3A shows the measure of paw withdrawal threshold.
Figure 3B:
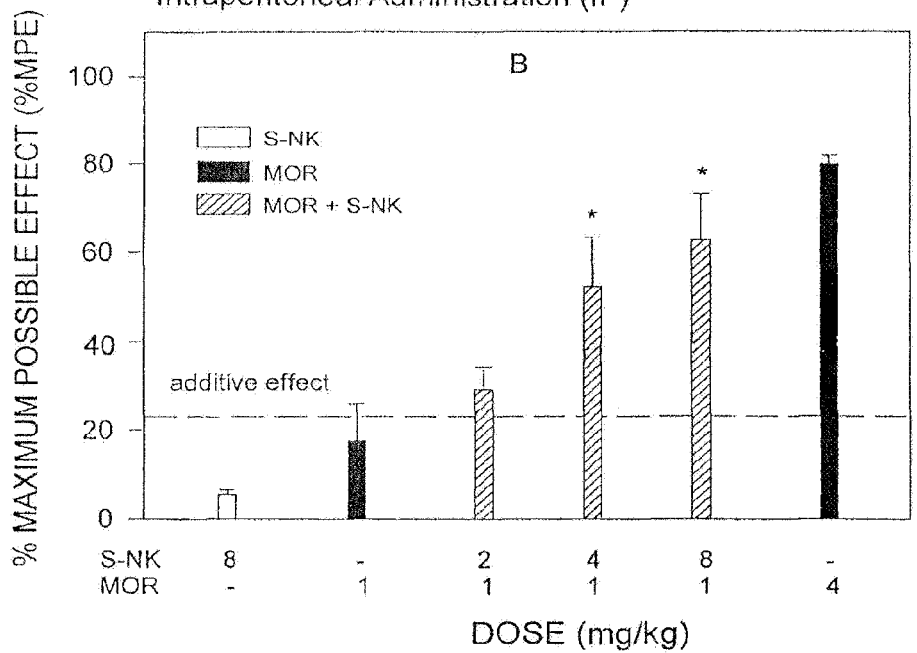
FIG. 3B shows the maximum possible effect.
Figure 4A:
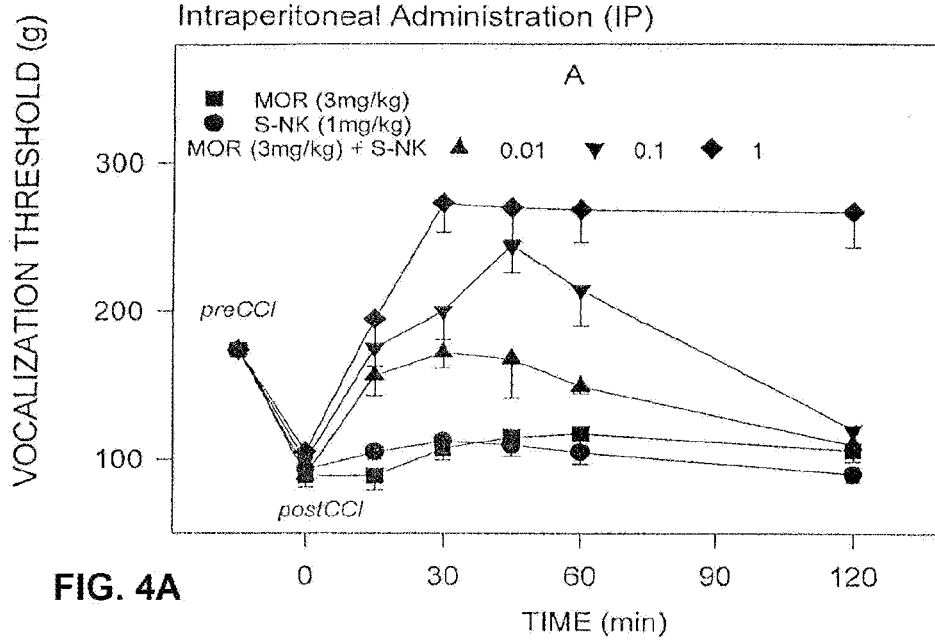
FIG. 4A shows the measure of vocalization threshold.
Figure 4B:
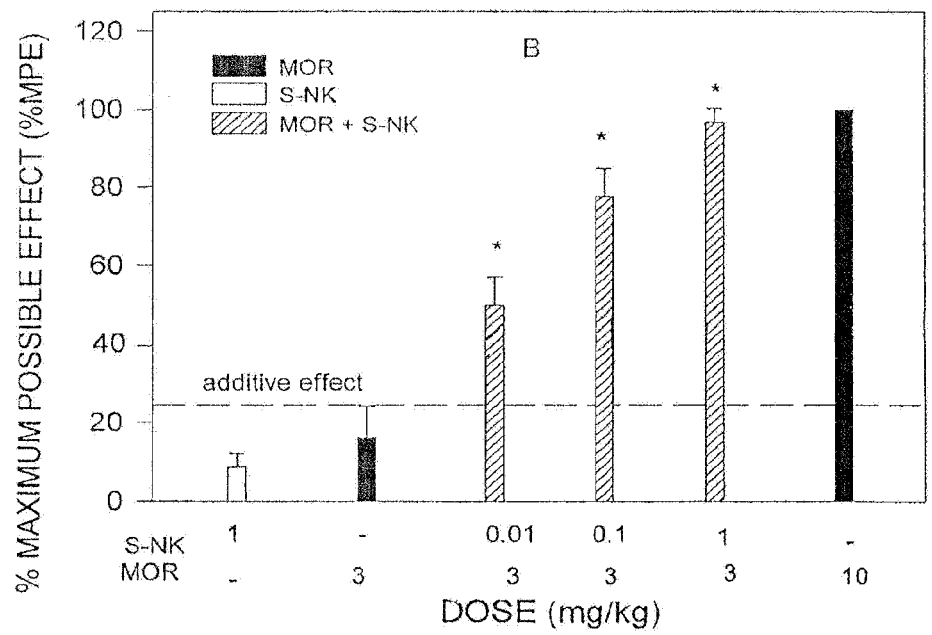
FIG. 4B shows the maximum possible effect.
Figure 5:
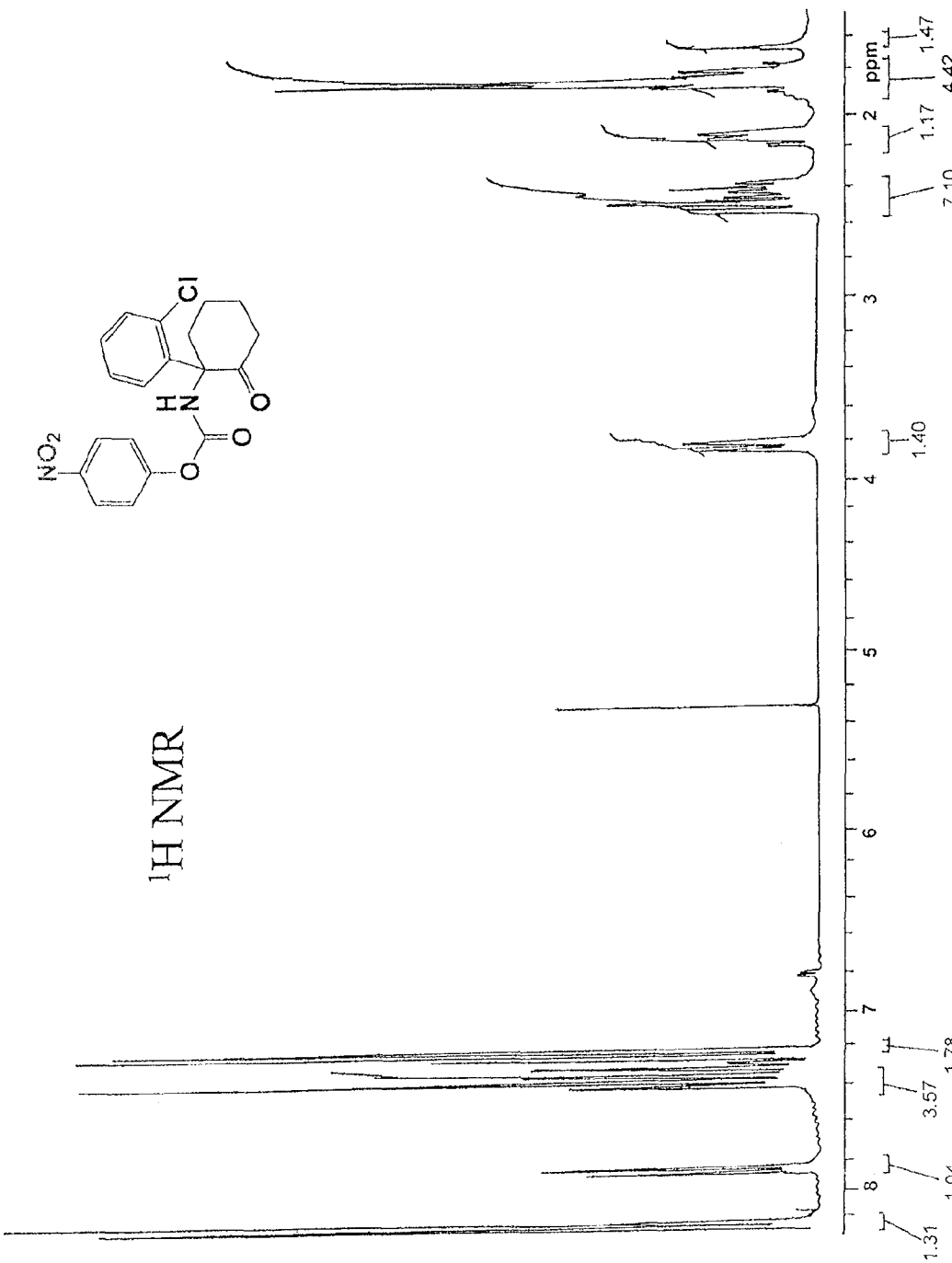
FIG. 5 shows H-NMR analysis of the para-nitrophenoxycarbamate of norketamine.
Figure 6:
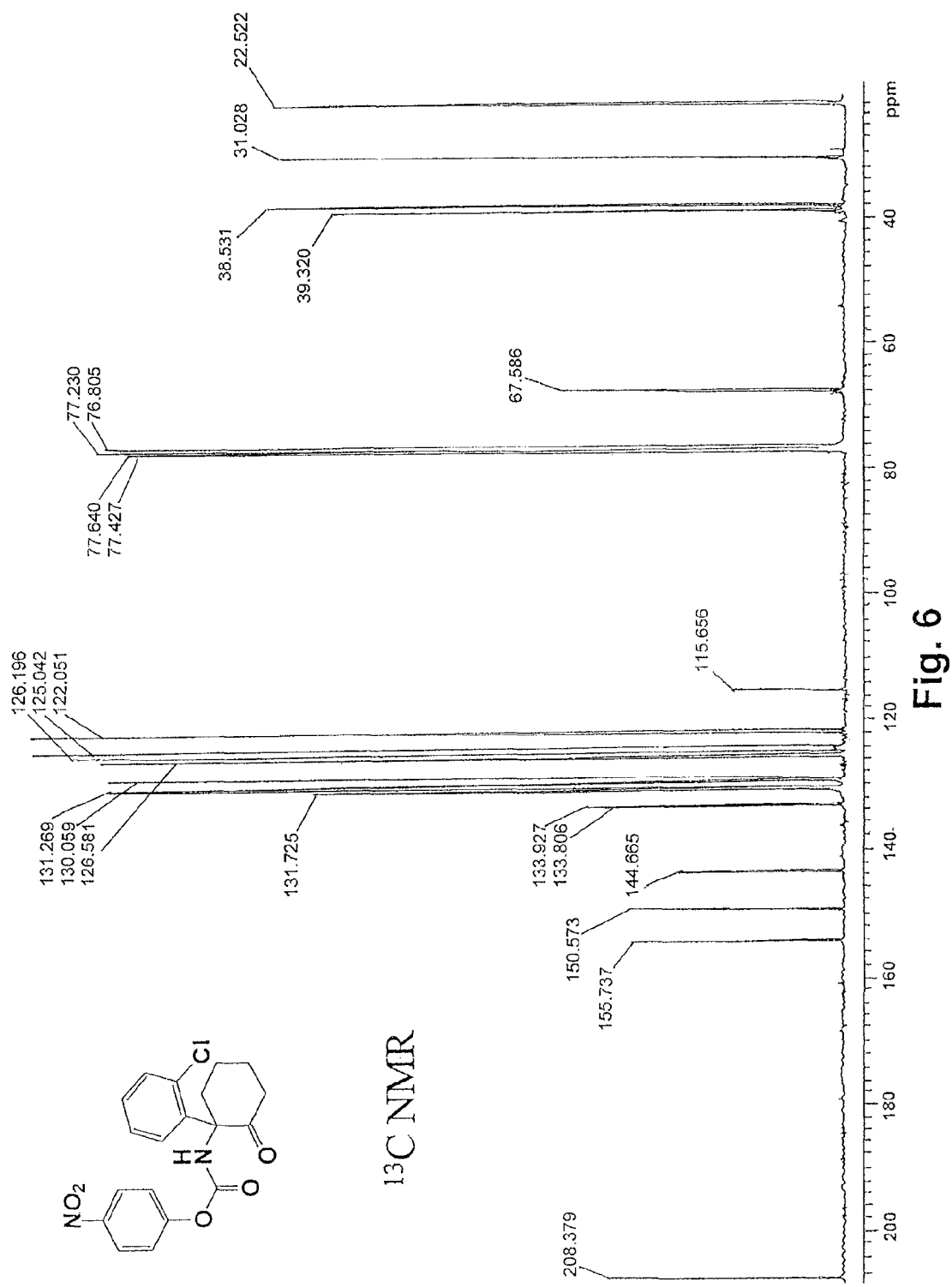
FIG. 6 shows C-NMR analysis of para-nitrophenoxycarbamate of norketamine.
Figure 7:
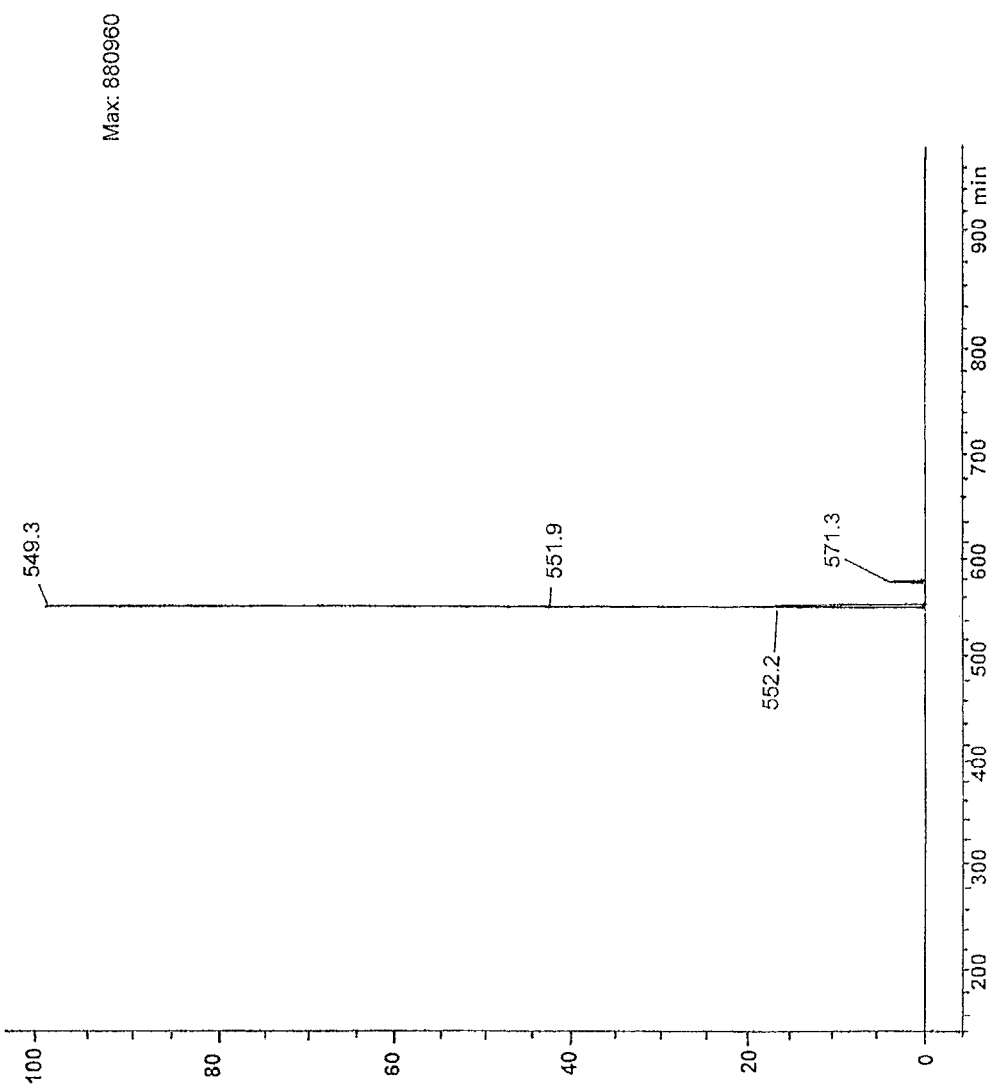
FIG. 7 shows ESI-MS analysis of a codeine racemic-norketamine codrug.

Embodiments of the present invention include novel synergistic opioid-ketamine and norketamine codrug combinations. Additional embodiments include methods of treating and preventing pain in a subject, comprising administration of a codrug combination of the present invention, as well as methods of synthesizing the codrugs.

In accordance with this detailed description, the following abbreviations and definitions apply. It must be noted that as used herein, the singular forms "a", "an", and "the" include plural referents unless the context clearly dictates otherwise. Thus, for example, reference to "compounds" includes a plurality of such compounds and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless otherwise stated, the following terms used in the specification and claims have the meanings given below:

By "opioid" is meant any agent that binds to opioid receptors, found principally in the central nervous system and gastrointestinal tract. There are four broad classes of opioids: endogenous opioid peptides, produced in the body; opium alkaloids, such as morphine (the prototypical opioid) and codeine; semi-synthetic opioids such as heroin and oxycodone; and fully synthetic opioids such as pethidine and methadone that have structures unrelated to the opium alkaloids.

"Pharmaceutically acceptable carrier" means a carrier that is useful in preparing a pharmaceutical composition that is generally safe, non-toxic and neither biologically nor otherwise undesirable, and includes a carrier that is acceptable for human pharmaceutical use as well as veterinary use. "A pharmaceutically acceptable carrier" as used in the specification and claims includes both one and more than one such carrier.

As used herein, a "mammal" or "individual" refers to humans or animals such as dogs, cats, horses and the like and farm animals such as cows, pigs, guinea pigs and the like.

"Treating" or "treatment" of a disease and/or pain includes:
(1) preventing the disease/pain, i.e., causing the clinical symptoms of the disease not to develop in a mammal (preferable a human) that may be exposed to or predisposed to the disease but does not yet experience or display symptoms of the disease,
(2) inhibiting the disease/pain, i.e., arresting or reducing the development of the disease or its clinical symptoms, or
(3) relieving the disease/pain, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Pharmaceutically acceptable salt" refers to pharmaceutically acceptable salts of norketamine which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, fumarate, mesylate, acetate, maleate, oxalate and the like.

"Optional" or "optionally" means that the subsequently described event or circumstance may, but need not, occur, and that the description includes instances where the event or circumstance occurs and instances in which it does not.

The term "subject in need thereof" refers to any animal in need of relief from pain, or the same or similar symptoms caused by any other disease or condition. Preferably, the subject is a mammal. More preferably, the subject is human.

"Synergistic effect" and "supra-additive effect" refer to action of two agents such as drugs or chemicals producing an effect, in this case, analgesia, which is greater than the simple addition of the effects of each drug administered by themselves.

"Mammal" or "individual" refers to humans or animals such as dogs, cats, horses, and the like, and farm animals, such as cows, pigs, guinea pigs and the like.

As used herein, (including the claims), the term alkylene or alkylene group is to be understood in the broadest sense to mean hydrocarbon residues which can be linear, i.e., straight-chain, or branched, and can be acyclic or cyclic residues or comprise any combination of acyclic and cyclic subunits. Further, the term alkylene as used herein expressly includes saturated groups as well as unsaturated groups which latter groups contain one or more, for example, one, two, or three, double bonds and/or triple bonds. The term alkylene includes substituted and unsubstituted alkylene groups; one or more carbons may be replaced with heteroatoms O or S; and the alkylene may be pegylated. In accordance with the above substitutions, the alkylene is also understood to include all isomers, diastereiomers, enantiomers; and cis and trans geometrical isomers.

Examples of alkylene residues containing from 1 to 20 carbon atoms are methylene, ethylene, propylene, butylene, pentylene, hexylene, heptylene, octylene, nonylene, decylene, undecylene, dodecylene, tetradecylene, hexadecylene, octadecylene, and eicosylene, the n-isomers of all these residues, isopropylene, isobutylene, 1-methylbutylene, isopentylene, neopentylene, 2,2-dimethylbutylene, 2-methylpentylene, 3-methylpentylene, isohexylene, 2,3,4-trimethylhexylene, isodecylene, sec-butylene, tertbutylene, or tertpentylene. In certain preferred embodiments, the alkylene contains from 1 to 4 carbons.

Unsaturated alkylene residues are, for example, alkenylene residues such as vinylene, 1-propenylene, 2-propenylene (=allyl), 2-butenylene, 3-butenylene, 2-methyl-2-butenylene, 3-methyl-2-butenylene, 5-hexenylene, or 1,3-pentadienylene, or alkynylene residues such as ethynylene, 1-propynylene, 2-propynylene (=propargyl), or 2-butynylene. Alkylene residues can also be unsaturated when they are substituted.

Unless stated otherwise, the term alkylene preferably comprises acyclic saturated hydrocarbon residues containing from 1 to 6 carbon atoms which can be linear or branched. Additionally, included are acyclic unsaturated hydrocarbon residues containing from 2 to 6 carbon atoms which can be linear or branched like (C.sub.2-C.sub.6)-alkenylene and (C.sub.2-C.sub.6)-alkynylene, and cyclic alkylene groups containing from 3 to 8 ring carbon atoms, in particular from 3 to 6 ring carbon atoms. A particular group of saturated acyclic alkylene residues is formed by (C.sub.1-C.sub.4)-alkylene residues like methylene, ethylene, n-propylene, isopropylene, n-butylene, isobutylene, sec-butylene, and tert-butylene.

The present invention provides codrugs, compositions and synthetic methods wherein an opioid analgesic and ketamine or norketamine, or one of its enantiomers, are combined to produce a single chemical codrug entity. It is administered in amounts to produce a synergistic (greater than additive) analgesic response to pain. The pain may be acute, chronic, or cancer related. The codrugs of the present invention have a slower rate of development of opioid tolerance and dependence, with diminished clinical side effects than those seen with opioid-only therapies for pain.

Typical side effects known to occur following the administration of an N-methyl-D-asparate antagonist, such as norketamine, are diminished when the codrug is used; however, the analgesic activity is retained. The spectrum of treatable pain symptoms include nociceptive pain, such as low back pain and postsurgical pain, and neuropathic pain, such as diabetic neuropathy and AIDs related neuropathy. These pain symptoms are more effectively treated using the codrugs of the present invention more effectively than by treatment with opioids only.

The codrug of the present invention comprises two different drugs, which when combined have a synergistic analgesic effect in the form of a single chemical entity. The two drugs are connected directly or by means of a cleavable covalent linker, such as an ester, an amide, and a carbamate, which is cleaved in vivo to regenerate the individual drug entities at the desired site of action.

Ketamine (2-(2-chlorophenyl)-2-(methylamino)-cyclohexanone) is a general anesthetic used by anesthesiologists, veterinarians, and researchers. However, Ketamine is well known to have important clinical disadvantages. Particularly, ketamine is known to cause disturbing emergence reactions, including delirium, dysphoria, and unpleasant dreams (Leung et al., 1985, *J. Med. Chem.* 29: 2396-2399). Current pharmaceutical compositions of ketamine are racemic mixtures of S- and R-ketamine, though S-ketamine has been found recently to be twice as potent as R-ketamine and to allow faster recovery with fewer negative side effects than the racemic mixture (C. S. T. Aun, 1999, *Br. J. Anaesthesia* 83: 29-41). One of the principal metabolic products of ketamine is norketamine (2-(2-chlorophenyl)-2-amino-cyclohexanone). Ketamine has also been known also to have analgesic properties (Domino et al., 1965, *Clin. Pharmacol. Ther.* 6: 279); profound analgesia can be achieved with subanesthetic doses of ketamine (Bovill, 1971, *Br. J. Anaesth.* 43: 496; Sadove et al., 1971, *Anesth. Analg.* 50: 452-457).

Studies have shown that ketamine is converted metabolically through demethylation to norketamine, in vivo, at rates dependent on the route of administration, with oral and rectal administrations having the fastest rates due to a high degree of first pass metabolism in the liver (see, e.g., Grant et al., 1981, Br. J. Anaesth. 53: 805-810; Grant et al., 1981, *Br. J. Anaesth.* 55: 1107-1111; Leung et al., 1985, *J. Med. Chem.* 29: 2396-2399; Malinovsky et al., 1996, *Br. J. Anaesthesia* 77: 203-207). Norketamine binds the NMDA receptor less tightly than either S- or R-ketamine (Ebert et al., 1997, *Eur. J. Pharm.* 333: 99-104) and norketamine is speculated to have an anesthetic and analgesic potency one third that of ketamine (C. S. T. Aun, 1999, *Br. J. Anaesthesia* 83: 29-41), perhaps explaining the absence of administration of norketamine as an analgesic in the prior art.

Initial studies suggest that norketamine produces stereoselective effects on locomotor activity, schedule-controlled operant responding, abuse liability and autonomic side effects [Dwoskin et al., 1999; Risner et al., 1988; Stairs et al., (in press)]. This suggests that it may be possible to separate the desirable effect (analgesic) from the undesirable side effects of ketamine.

The structures of R- and S-norketamine are presented below:

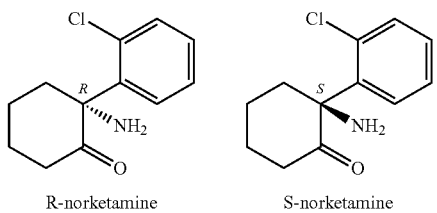

R-norketamine        S-norketamine

The present invention relates to pharmaceutical compositions and synthetic methods wherein an opioid analgesic and a ketamine or a norketamine, including S-norketamine, R-norketamine, and racemic norketamine and S-ketamine, R-ketamine and racemic ketamine, are combined to produce a single chemical co-drug entity and administered in amounts to produce a synergistic analgesic response to pain, including acute, chronic and/or cancer-related pain.

The codrugs of the present invention have a slower rate of opioid tolerance development and dependence with diminished clinical side effects than typically observed with conventional opioid only therapy for pain. Typical side effects known to occur following administration of ketamine and norketamine are also expected to be diminished.

Codrugs of the present invention comprise an opioid and a ketamine or a norketamine within a single chemical entity. The two drugs may be connected directly or by means of a cleavable covalent linker (e.g., ester, carbonate, amide, carbamate, etc.) which is cleaved in vivo upon administration to regenerate the active drug entities. By providing two drugs as a single entity, instead of as a physical mixture, the codrugs of the present invention provide advantages including improved drug stability, improved targeting of drugs to the site of action and a more desirable pharmacokinetic properties. This is especially true for drugs with differing physiochemical properties, such as lipid solubility.

When the opioid and the norketamine are linked together and administered as a co-drug, these molecules would undergo the same pharmacokinetics prior to cleavage. Specifically, where different molecules have substantially different partition coefficients, absorption across membranes would be the same. Other advantages of administering different molecules as co-drugs is described in *Synthesis and Hydrolytic Behavior of Two Novel Tripartate Codrugs of Naltrexone and 6β-Naltrexone with Hydroxybupropion as Potential Alcohol Abuse and Smoking Cessation Agents*, Hamad et al., *Bioorganic and Medicinal Chemistry*, 2006, volume 14, pages 7051-7061; the disclosure of which is hereby incorporated by reference in its entirety.

The present invention provides a codrug of the following formula:

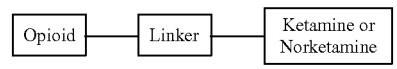

wherein the linker is selected from the group consisting of the following formulas:

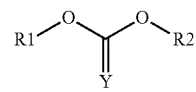

wherein Y is O or S; and R1-O is an opioid moiety and R2-N—R3 is a norketamine (R3=H) or ketamine (R3=CH$_3$) moiety

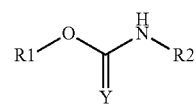

wherein X is a bond, O, S, NH, NR4 (R4=alkyl), (CH$_2$)$_x$ (where x=1-20, and the alkane moiety can be linear or branched), and wherein R2-N—R3 is a norketamine moiety (R3=H) or a ketamine moiety (R3=CH$_3$), and R1-O is an opioid moiety.

One embodiment of the present invention is a composition of the following formula:

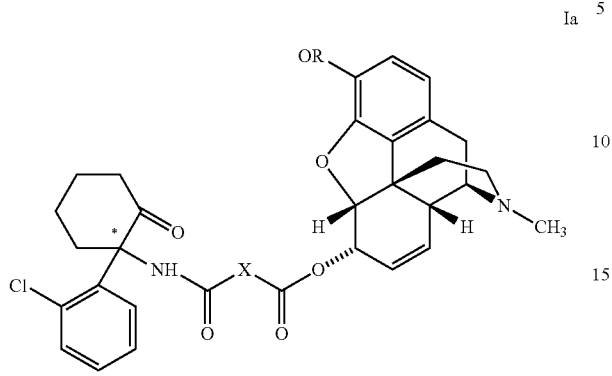

Ia and compositions thereof, and compositions thereof, wherein X is a bond, O, S, NH, NR1 (R1=alkyl), $(CH_2)_x$ (x=1-20, and the alkane moiety can be linear or branched), R=H, $CH_3$, R—CO— (where R=alkyl), and where * indicates the racemic, S- or R-form of the norketamine moiety.

Another embodiment of the present invention is a composition of the following formula:

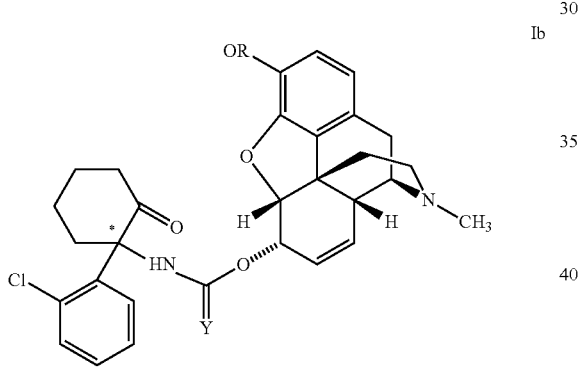

Ib and compositions thereof, wherein Y=O, S, and R=H, $CH_3$, RCO— (where R=alkyl) and * indicates racemic, S- or R-form of norketamine.

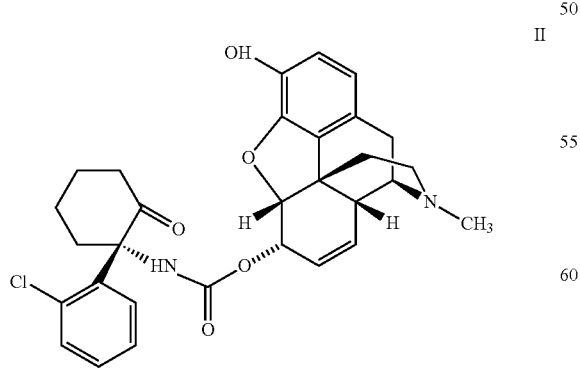

II

The compound of formula II is a S-norketamine:morphine codrug.

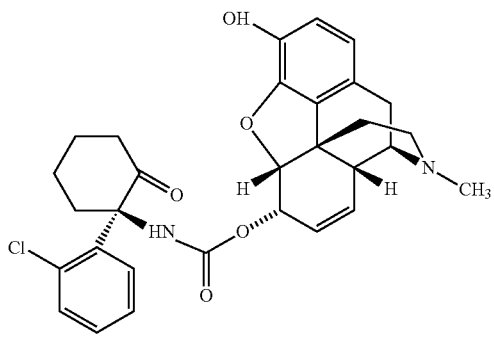

III

The compound of formula III is a R-norketamine:morphine codrug

Codrugs of the present invention may include a codrug comprising codeine linked with racemic norketamine as shown:

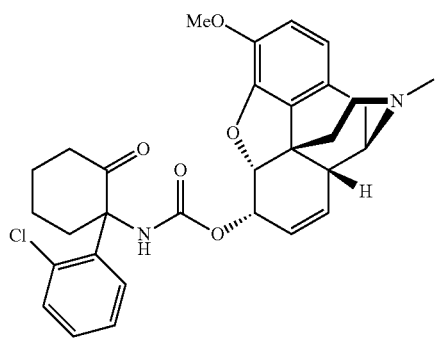

Codrugs of the present invention may also include a codrug comprising codeine linked with racemic ketamine as shown:

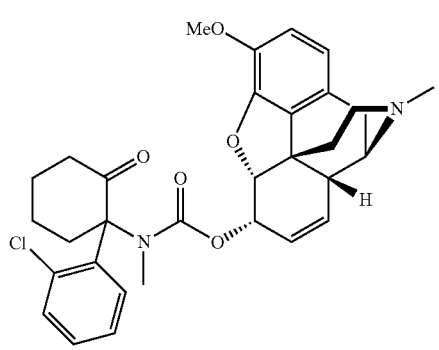

Other codrugs may include, but are not limited to, a codrug wherein S-ketamine is linked to morphine by a carbamate linker; a codrug wherein S-ketamine is linked to codeine by a carbamate linker; a codrug wherein S-ketamine is linked to oxycodone by a carbamate linker; a codrug wherein S-ketamine is linked to 3-acetylmorphine by a carbamate linker; a codrug wherein S-ketamine is linked to oxymorphone by a carbamate linker; a codrug wherein S-ketamine is linked to hydromorphone by a carbamate linker; a codrug wherein S-ketamine is linked to butorphenol by a carbamate linker; a codrug wherein S-ketamine is linked to bupernorphine by a carbamate linker; a codrug wherein S-ketamine is linked to tramadol by a carbamate linker; and a codrug wherein S-ketamine is linked to levorphanol by a carbamate linker.

Other codrugs may include, but are not limited to, a codrug wherein S-norketamine is linked to morphine by a carbamate linker; a codrug wherein S-norketamine is linked to codeine by a carbamate linker; a codrug wherein S-norketamine is linked to oxycodone by a carbamate linker; a codrug wherein S-norketamine is linked to 3-acetylmorphine by a carbamate linker; a codrug wherein S-norketamine is linked to oxymorphone by a carbamate linker; a codrug wherein S-norketamine is linked to hydromorphone by a carbamate linker; a codrug wherein S-norketamine is linked to butorphenol by a carbamate linker; a codrug wherein S-norketamine is linked to bupernorphine by a carbamate linker; a codrug wherein S-norketamine is linked to tramadol by a carbamate linker; and a codrug wherein S-norketamine is linked to levorphanol by a carbamate linker.

Examples of opioids for combination with norketamine include all therapeutically useful and pharmacologically active opioids and opioid metabolites and their respective pure enantiomers and/or diastereiomers. Representative examples include but are not limited to dihydroetorphine, butorphanol, pentazocine, morphine, phenazocine, hydromorphone, codeine, 3-acetylmorphine, oxymorphone, methadone, propoxyphene, oxycodone, tramadol, hydrocodone, buprenorphine, levorphanol, dihydrocodeine, L-acetylmethadol, ethylmorphine, nalbuphine, etorphine, buprenorphine, normethadone, dihydromorphine, noroxycodone, normorphine, norlevorphanol.

In certain embodiments, the general multi-step synthetic procedure for preparation of the codrug includes: reacting para-nitrophenyl chloroformate with an opiate drug containing a hydroxy group in the presence of triethyl amine and dry chloroform and the solution is cooled to 0 degrees C. The resulting 6-O-para-nitrophenoxycarbonate ester of an opiate drug is then reacted with a norketamine to yield the ketamine-opioid or norketamine-opioid codrug.

Generally speaking the opioids and ketamine or norketamine of the present invention that are synthesized into codrugs in accordance with the present invention will contain a free hydroxyl group or another equivalent moiety capable of being acylated. Examples of other moieties include primary or secondary amines, or carbonyl containing moieties. Example of opioids suitable for synthesis of the codrugs in accordance with the present invention include dihydroetorphine, butorphanol, pentazocine, morphine, 3-acetylmorphine, phenazocine, hydromorphone, codeine, oxymorphone, methadone, propoxyphene, oxycodone, tramadol, hydrocodone, buprenorphine, levorphanol, dihydrocodeine, L-acetylmethadol, ethylmorphine, nalbuphine, etorphine, buprenorphine, normethadone, dihydromorphine, noroxycodone, normorphine, norlevorphanol, as well as any pharmaceutically acceptable salts, metabolites, enantiomers and diastereiomers thereof.

S-norketamine, R-norketamine, and racemic norketamine, as well as S-ketamine, R-ketamine, and racemic ketamine, are suitable for use in the present invention.

Compositions of the present invention can be synthesized using the methods readily available to the skilled artisan, including those methods known in the art of synthetic organic chemistry, or variations thereon as readily appreciated and readily performable by those skilled in the art. Moreover, the synthesis methods known in the art are not intended to comprise a comprehensive list of all means by which the compositions described and claimed in this patent application may be synthesized. Some of the compounds of the invention may have stereogenic centers. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diasteriomeric mixture of isomers. Thus, when using the term "compound", it is understood that all stereoisomers are included.

The compounds of the present invention may be obtained or used as inorganic or organic salts using methods known to those skilled in the art. It is well known to one skilled in the art that an appropriate salt form is chosen based on physical and chemical stability, flowability, hydroscopicity and solubility. Pharmaceutically acceptable salts of the present invention with an acidic moiety may be optionally formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be optionally formed from organic and inorganic acids.

For example salts may be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. The compounds can also be used in the form of esters, carbamates and other conventional prodrug forms, which when administered in such form, convert to the active moiety in vivo. When using the term "compound" herein, it is understood that all salts are included.

The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like. Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference in its entirety.

The codrugs and compositions and formulations thereof effective compounds may be administered alone or in conjunction with other pharmaceutically active compounds. It will be understood by those skilled in the art that pharmaceutically active compounds to be used in combination with the compounds described herein will be selected in order to avoid adverse effects on the recipient or undesirable interactions between the compounds. As used herein, the term "active ingredient" or "active agent" is meant to include compounds described herein when used alone or in combination with one or more additional pharmaceutically active compounds. The amount of the compounds described herein required for use in the various treatments of the present invention depend, inter alia, on the route of administration, the age and weight of the animal (e.g. human) to be treated and the severity of the condition being treated.

The compositions of the present invention and such second therapeutic agent can be administered separately or as a physical combination in a single dosage unit, in any dosage form and by various routes of administration, as described above. The compositions of the present invention may be formulated together with the second therapeutic agent in a single dosage unit (that is, combined together in one dosage form). When the compositions of the present invention and the second therapeutic agent are not formulated together in a single dosage unit, they may be administered essentially at the same time, or in any order; for example, the compositions of the present invention may be administered first, followed by administration of the second agent.

Formulations

It is preferred to administer the codrugs of the present invention as pharmaceutical formulations. Useful formulations comprise a codrug and one or more pharmaceutically acceptable carriers. The term "pharmaceutically acceptable" means compatible with the other ingredients of the formulation and not toxic to the recipient. Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

In general, the codrugs of the subject invention will be administered in a therapeutically effective amount by any of the accepted modes of administration for agents that serve similar utilities. Such compositions are prepared in a manner well known in the pharmaceutical art. In one probable mode of administration, the codrug will be administered by the oral route.

The actual amount of the codrug will depend on a number of factors, such as the severity of the pain to be treated, the age and relative health of the subject, the potency of the agent used, the route and form of administration, and other factors. Toxicity and therapeutic efficacy of such compounds can be determined by standard pharmaceutical procedures in vitro or in experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Data obtained in vitro and in animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. A dose may be formulated in animal models to achieve a circulating plasma concentration range which includes the $ED_{50}$ (i.e., the dose of the test compound which achieves a half-maximal inhibition of symptoms). Such information can be used to more accurately determine useful doses in humans. Levels in plasma may be measured, for example, by high performance liquid chromatography.

In preparing the compositions of this invention, the codrug may be mixed with an excipient, diluted by an excipient or enclosed within a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The quantity of codrug in the pharmaceutical composition and unit dosage form thereof may be varied or adjusted widely depending upon the particular application, the manner or introduction, the potency of the particular compound, and the desired concentration. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The codrug is effective over a wide dosage range and is generally administered in a pharmaceutically or therapeutically effective amount. It will be understood, however, that the amount of the codrug actually administered will be determined by a physician, in the light of the relevant circumstances, including the condition to be treated, the severity of the disease being treated, the chosen route of administration, the actual compound administered, the age, weight, and response of the individual patient, the severity of the patient's symptoms, and the like. Typically, the physician will administer the compound until a dosage is reached that achieves the desired effect.

The codrugs of the invention will be administered in a therapeutically effective amount by any of the accepted modes of administration. The codrugs can be administered by a variety of routes, including, but not limited to, oral, parenteral (e.g., subcutaneous, intravenous, intramuscular, intraperitoneal, intraarterial), intralesional, neuroaxial (epidural, intrathecal, intracerebral), topical, intranasal, localized (e.g., surgical application or surgical suppository), sublingual, submucosal, rectal, vaginal, pulmonary (e.g., aerosols, inhalation, or powder) and transdermal routes of administration. The compounds can be administered continuously by infusion or by bolus injection. Such compositions are prepared in a manner well known in the pharmaceutical art.

The actual amount of the codrug of the subject invention will depend on a number of factors, such as the severity of the pain and/or condition, i.e., the condition or disease to be treated, the age and relative health of the subject, the potency of the compound used, the route and form of administration, and other factors.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending physician depending upon factors such as the severity of the pain, the age, weight and general condition of the patient, and the like.

The compositions administered to a patient are in the form of pharmaceutical compositions described supra. These compositions may be sterilized by conventional sterilization techniques, or may be sterile filtered. When employed as pharmaceuticals, the compounds of the subject invention are usually administered in the form of pharmaceutical compositions. This invention also includes pharmaceutical compositions, which contain as the active ingredient, one or more of the compounds of the subject invention above, associated with one or more pharmaceutically acceptable carriers or excipients. The excipient employed is typically one suitable for administration to human subjects or other mammals.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and/or flavoring agents. By way of example, for preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. The compositions of the invention can be formulated so as to provide rapid, sustained or delayed release of the active ingredient after administration to the patient by employing procedures known in the art.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, alcohol, and cellulose acetate.

The preferred parenteral form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Also included may be carrier molecules such as proteoglycans. Specific examples of such carrier molecules include, but are not limited to, glycosaminoglycans such as heparin sulfate, hyaluronic acid, keratan-sulfate, chondroitin 4-sulfate, chondroitin 6-sulfate, heparan sulfate and dermatin sulfate, perlecan, and pento polysulfate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions may be administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The codrugs of this invention may be administered in a sustained release form. Suitable examples of sustained-release preparations include semipermeable matrices of solid hydrophobic polymers, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res. 15: 167-277 (1981) and Langer, Chem. Tech. 12: 98-105 (1982) or poly(vinyl alcohol)), polylactides (U.S. Pat. No. 3,773,919), copolymers of L-glutamic acid and gamma ethyl-L-glutamate (Sidman et al., Biopolymers 22: 547-556, 1983), non-degradable ethylene-vinyl acetate (Langer et al., supra), degradable lactic acid-glycolic acid copolymers such as the LUPRON DEPOT™ (i.e. injectable microspheres composed of lactic acid-glycolic acid copolymer and leuprolide acetate), and poly-D-(−)-3-hydroxybutyric acid (EP 133,988). The compounds of this invention can be administered in a sustained release form, for example a depot injection, implant preparation, or osmotic pump, which can be formulated in such a manner as to permit a sustained release of the active ingredient. Implants for sustained release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host. The implant is placed in proximity to the site of protein deposits (e.g., the site of formation of amyloid deposits associated with neurodegenerative disorders), so that the local concentration of active agent is increased at that site relative to the rest of the body.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

The dosage when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. The proper dosage of a composition of the present invention when administered in combination with the second therapeutic agent will be readily ascertainable by a medical practitioner skilled in the art, once armed with the present disclosure. Upon improvement of a patient's condition, a maintenance dose of a composition of the present invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of pain.

The compounds recited herein are presented for exemplary purposes only, and should not be construed as being a limited presentation of compounds of the present invention.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Examples be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

EXAMPLES

Example 1

Preparation of a Codeine-Racemic Norketamine Codrug

Procedure for the Synthesis of Para-Nitrophenoxycarbamate of Norketamine.

To a mixture of norketamine (0.05 g, 0.22 mmol) in anhydrous toluene (2 mL) and $Na_2CO_3$ (0.082 g) was added a solution of para-nitrophenyl chloroformate (0.129 g, 0.64 mmol) in anhydrous toluene (2 mL). After heating for 8 hours at 85° C., the reaction mixture was cooled to room temperature and filtered. Toluene was evaporated under vacuum and the reaction mixture was diluted with dichloromethane (DCM). The DCM layer was washed 6 times with 50% aqueous NaHCO3 solution to remove the para-nitrophenol side-product and then with brine. The DCM layer was then dried over anhydrous sodium sulfate, filtered, concentrated under vacuum to afford the para-nitrophenoxycarbamate of norketamine as a pale solid. $^1$H-NMR ($CDCl_3$): δ 8.17 (2H, dd), 7.87 (1H, d), 7.37 (3H, m) 7.23 (2H, dd), 3.84 (1H, d), 2.55-1.71 (8H).

Scheme 1$^a$

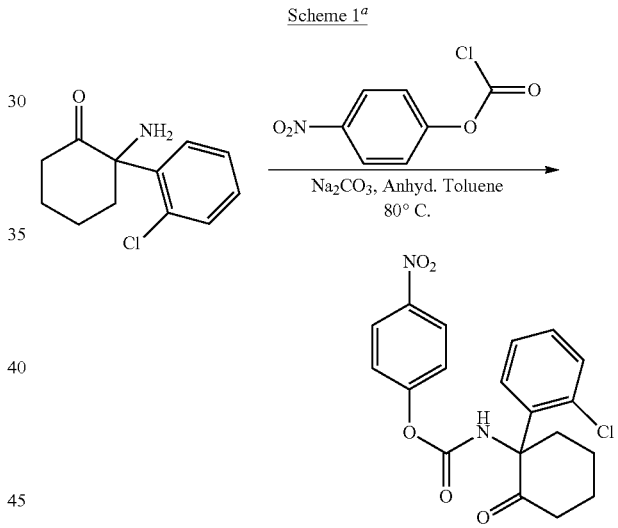

Procedure for the Synthesis Codeine-Racemic-Norketamine Codrug.

In second step, the hybrid drug of codeine and racemic-norketamine was synthesized in the following way. All glassware was oven-dried and then cooled under a nitrogen atmosphere. 51 mg (0.17 mmol) of codeine was placed in a round-bottom flask under a nitrogen atmosphere and dissolved in 2 mL of dry THF. The solution was cooled to 0° C. in an ice-bath. 8 mg (0.19 mmol) of NaH was added and the mixture was allowed to stir for 5 minutes. 55 mg (0.14 mmol) of the para-nitrophenoxycarbamate of norketamine was dissolved in 4 mL of dry THF and the resulting solution was added dropwise to the reaction mixture; the reaction mixture was allowed to warm to room temperature. The progress of the reaction was monitored by TLC. After the reaction was complete, the reaction mixture was first passed through a pad of celite and then concentrated under vacuum and then diluted with chloroform. The chloroform layer was washed 3 times with 50% aqueous $NaHCO_3$ solution and once with brine. The chloroform layer was dried over anhydrous $Na_2SO_4$, filtered, and then concentrated under vacuum to afford the hybrid drug of codeine and racemic-norketamine as an amorphous solid. Column chromatography was used to get the diastereomeric mixture of the two codeine-norketamine codrugs. MS (ESI) m/z 549 (M+H)+.

Scheme 1[b]

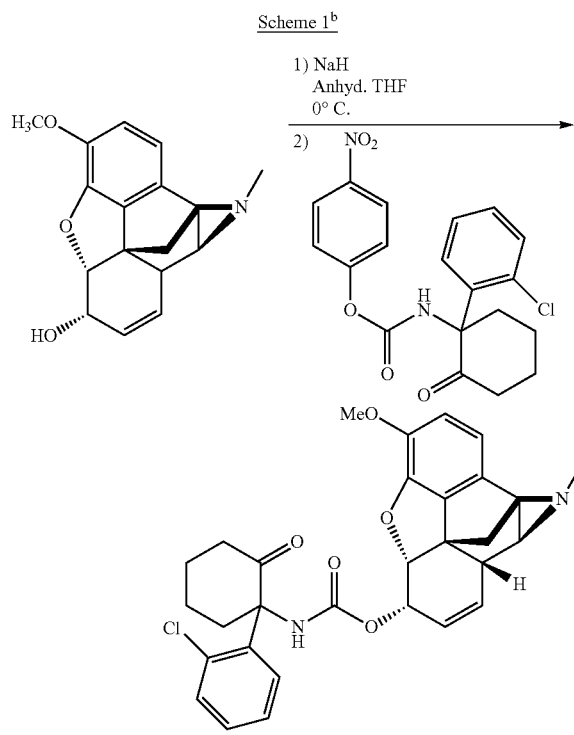

Example 2

Preparation of a Codeine-Racemic Ketamine Codrug

Procedure for the Synthesis of Para-Nitrophenoxycarbamate of Ketamine.

To a mixture of ketamine (0.052 g, 0.22 mmol) in anhydrous toluene (2 mL) and $Na_2CO_3$ (0.082 g) was added a solution of para-nitrophenyl chloroformate (0.129 g, 0.64 mmol) in anhydrous toluene (2 mL). After heating for 8 hours at 100° C., the reaction mixture was cooled to room temperature and filtered. Toluene was evaporated under vacuum and the reaction mixture was diluted with dichloromethane (DCM). The DCM layer was washed 6 times with 50% aqueous $NaHCO_3$ solution to remove the para-nitrophenol side-product and then with brine. The DCM layer was then dried over anhydrous sodium sulfate, filtered, concentrated under vacuum to afford the para-nitrophenoxycarbamate of ketamine as a pale solid. MS (ESI) m/z 403 (M+H)+.

Scheme 1[a]

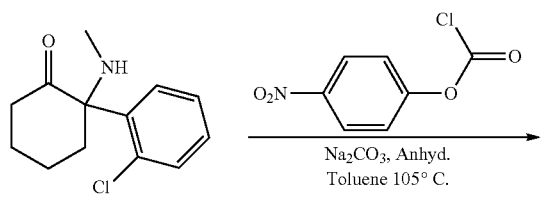

-continued

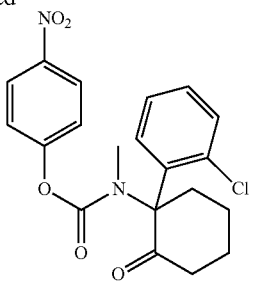

Procedure for the Synthesis Codeine-Racemic-Ketamine Codrug.

In second step, the hybrid drug of codeine and racemic-ketamine was synthesized in the following way. All glassware was oven-dried and then cooled under a nitrogen atmosphere. 51 mg (0.17 mmol) of codeine was placed in a round-bottom flask under a nitrogen atmosphere and dissolved in 2 mL of dry THF. The solution was cooled to 0° C. in an ice-bath. 8 mg (0.19 mmol) of NaH was added and the mixture was allowed to stir for 5 minutes. 56 mg (0.14 mmol) of the para-nitrophenoxycarbamate of ketamine was dissolved in 4 mL of dry THF and the resulting solution was added dropwise to the reaction mixture; the reaction mixture was allowed to warm to room temperature. The progress of the reaction was monitored by TLC. After the reaction was complete, the reaction mixture was first passed through a pad of celite and then concentrated under vacuum and then diluted with chloroform. The chloroform layer was washed 3 times with 50% aqueous $NaHCO_3$ solution and once with brine. The chloroform layer was dried over anhydrous $Na_2SO_4$, filtered, and then concentrated under vacuum to afford the hybrid drug of codeine and racemic-ketamine as an amorphous solid. Column chromatography was used to get the diastereomeric mixture of the two codeine-ketamine codrugs. MS (ESI) m/z 563 (M+H)+.

Scheme 1[b]

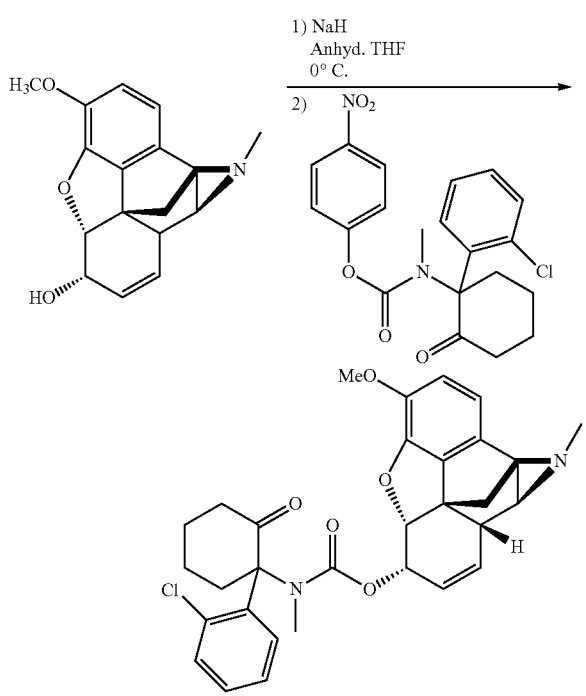

Example 2

Morphine+(+) Norketamine

| Male Rats 5-8 | | |
|---|---|---|
| day 1 | Rats 5, 6 | MOR 3 mg/kg + SAL |
| day 1 | Rats 7, 8 | MOR 3 mg/kg + (+) Norket 3mg/kg |

1) Solution MOR 3 mg/ul (the same Mor. Sal. than has been used today for Mor+(−) NK combination study, see p. 1)
2) (+) Norketamine 3 mg/ml dose 3 mg/kg inj. 1 ml/kg
   (+) Norketamine 6 mg in 2 ml (3 mg/ml)
   (+) Norketamine HCl bottle #3 0.0069

| Day 1 | Bwt. | |
|---|---|---|
| Rat 5 | 385 g | 0.385 ml MOR + 0.385 ml SAL |
| Rat 6 | 392 g | 0.392 ml MOR + 0.392 ml SA |
| Rat 7 | 400 g | 0.40 ml MOR + 0.40 ul (+) NK |
| Rat 8 | 455 g | 0.455 ml MOR + 0.455 ul (+) NK |

| Rat | Baseline | Baseline | Inject Time | 15 min. | 30 min. | 60 min. | 120 min. |
|---|---|---|---|---|---|---|---|
| 5 | 1.45 | 1.50 | 1:58 | 3.24 | 5.72 | 1.93 | 1.61 |
| 6 | 1.36 | 1.24 | 1:59 | 3.55 | 6.2 | 4.50 | 5.44 |
| 7 | 1.35 | 1.41 | 2:01 | 10.0 | 10.0 | 6.34 | 8.58 |
| 8 | 1.38 | 1.40 | 2:02 | 10.0 | 10.0 | 10.0 | 5.43 |

Morphine & (−) Norketamine

| Male Rats #1-4 | | |
|---|---|---|
| Day 2 | Rats 1, 2 | Mor 3 mg/kg & (−) Norketamine 3 mg/kg |
| Day 2 | Rats 3, 4 | 3 mg/kg Mor & Saline |

TFL—intensity 40%, idle activity 5%, cut-off 10 sec.
Solutions
  1) Morphine—see p. 1
  2) (−) Norketamine—see p. 1

| Day 2 | Bwt. | |
|---|---|---|
| Rat 1 | 398 g | 0.398 ml Mor & 0.398 ml (−) NK |
| Rat 2 | 423 g | 0.423 ml Mor & 0.423 ml (−) NK |
| Rat 3 | 425 g | 0.425 ml Mor & 0.425 ml Saline |
| Rat 4 | 377 g | 0.377 ml Mor & 0.377 ml Saline |

| Rat | Baseline | Baseline | Inject Time | 15 min. | 30 min. | 60 min. | 120 min. |
|---|---|---|---|---|---|---|---|
| 1 | 1.63 | 1.52 | 1:10 | 1.83 | 2.27 | 2.53 | 2.37 |
| 2 | 1.43 | 1.56 | 1:11 | 2.60 | 3.50 | 3.81 | 3.17 |
| 3 | 1.70 | 1.68 | 1:13 | 2.03 | 2.74 | 1.94 | 1.48 |
| 4 | 1.75 | 1.60 | 1:14 | 4.89 | 7.26 | 6.84 | 5.37 |

Morphine & (+) Norketamine

| Male Rats #5-8 | | |
|---|---|---|
| Day 2 | Rats 5, 6 | 3 mg/kg Mor & 3 mg/kg (+) Norketamine |
| Day 2 | Rats 7, 8 | 3 mg/kg Mor & Saline |

TFL—Intensity 40%, idle activity 5%, cut-off 10 sec.
Solutions
  1) Morphine—see p. 2
  2) (+) Norketamine—see p. 2

| Day 2 | Bwt. | |
|---|---|---|
| Rat 5 | 389 g | 0.398 ml Mor & 0.389 ml (+) − NK |
| Rat 6 | 393 g | 0.393 ml Mor & 0.393 ml (+) − NK |
| Rat 7 | 398 g | 0.398 ml Mor & 0.398 ml SAL |
| Rat 8 | 458 g | 0.458 ml Mor & 0.458 ml SAL |

| Rat | Baseline | Baseline | Inject Time | 15 min. | 30 min. | 60 min. | 120 min. |
|---|---|---|---|---|---|---|---|
| 5 | 1.95 | 1.67 | 2:20 | 2.84 | 3.35 | 4.85 | 4.07 |
| 6 | 1.44 | 1.49 | 2:21 | 5.20 | 6.17 | 5.32 | 3.35 |
| 7 | 1.48 | 1.85 | 2:23 | 3.41 | 4.09 | 4.03 | 2.94 |
| 8 | 2.63 | 2.42 | 2:24 | 3.48 | 3.22 | 3.01 | 2.12 |

| Male Rats 1-4 | | |
|---|---|---|
| Day 1 | Rats 1, 2 | 3 mg/kg Morphine & Saline |
| Day 1 | Rats 3, 4 | 3 mg/kg Morphine & 3 mg/kg (−) Norketamine |

TFL—Intensity 40%, idle activity 5%, cut-off 10 sec.
Solutions
  1) Morphine—see p. 1
  2) (−) Norketamine—see p. 1

| Day 1 | Bwt. | |
|---|---|---|
| Rat 1 | 424 g | 0.424 ml Mor & 0.424 ml Saline |
| Rat 2 | 407 g | 0.407 ml Mor & 0.407 ml Saline |
| Rat 3 | 433 g | 0.433 ml Mor & 0.433 ml (−) NK |
| Rat 4 | 398 g | 0.398 ml Mor & 0.398 ml (−) NK |

| Rat | Baseline | Baseline | Inject Time | 15 min. | 30 min. | 60 min. | 120 min. |
|---|---|---|---|---|---|---|---|
| 1 | 1.60 | 1.52 | 1:45 | 2.92 | 3.64 | 3.28 | 2.74 |
| 2 | 1.48 | 1.40 | 1:45 | 1.82 | 2.36 | 3.30 | 1.92 |
| 3 | 1.42 | 1.36 | 1:46 | 2.37 | 2.28 | 1.99 | 1.37 |
| 4 | 2.01 | 1.66 | 1:46 | 5.06 | 5.04 | 4.89 | 1.97 |

Morphine & (+) Norketamine

| Male Rats 5-8 | | |
|---|---|---|
| Day 1 | Rats 5, 6 | 3 mg/kg Morphine & Saline |
| Day 1 | Rats 7, 8 | 3 mg/kg Morphine & 3 mg/kg (+) Norketamine |

TFL—Intensity 40%, idle activity 5%, cut-off 10 sec.
Solutions
  1) Morphine—see p. 1
  2) (+) Norketamine—see p. 2

| Day 1 | Bwt. | |
|---|---|---|
| Rat 5 | 430 g | 0.430 ml Mor & 0.430 ml Saline |
| Rat 6 | 414 g | 0.414 ml Mor & 0.414 ml Saline |
| Rat 7 | 431 g | 0.431 ml Mor & 0.431 ml (+) NK |
| Rat 8 | 400 g | 0.400 ml Mor & 0.400 ml (+) NK |

| Rat | Baseline | Baseline | Inject Time | 15 min. | 30 min. | 60 min. | 120 min. |
|---|---|---|---|---|---|---|---|
| 5 | 1.73 | 2.00 | 1:50 | 2.97 | 2.75 | 3.51 | 2.70 |
| 6 | 1.45 | 1.39 | 1:50 | 2.88 | 3.86 | 3.69 | 2.17 |
| 7 | 1.18 | 1.10 | 1:51 | 10.0 | 10.0 | 10.0 | 5.39 |
| 8 | 1.26 | 1.20 | 1:51 | 5.86 | 6.97 | 8.26 | 3.65 |

Morphine & (−) Norketamine

| Male Rats 1-4 | | |
|---|---|---|
| Day 2 | Rats 1, 2 | 3 mg/kg Morphine & (−) Norketamine |
| Day 2 | Rats 3, 4 | 3 mg/kg Morphine & Saline |

TFL—Intensity 40%, idle activity 5%, cut-off 10 sec.
Solutions
  1) Morphine—see p. 1
  2) (−) Norketamine—see p. 1

| Day 2 | Bwt. | |
|---|---|---|
| Rat 1 | 427 g | 0.427 ml Mor & 0.427 ml (−) Norketamine |
| Rat 2 | 410 g | 0.410 ml Mor & 0.410 ml (−) Norketamine |
| Rat 3 | 437 g | 0.437 ml Mor & 0.437 ml Saline |
| Rat 4 | 385 g | 0.385 ml Mor & 0.385 ml Saline |

| Rat | Baseline | Baseline | Inject Time | 15 min. | 30 min. | 60 min. | 120 min. |
|---|---|---|---|---|---|---|---|
| 1 | 1.37 | 1.30 | 10:30 | 2.83 | 4.17 | 3.47 | 2.19 |
| 2 | 1.41 | 1.45 | | 1.91 | 2.19 | 2.23 | 1.54 |
| 3 | 1.29 | 1.25 | 10:31 | 1.49 | 1.50 | 2.55 | 1.31 |
| 4 | 1.68 | 1.53 | | 2.85 | 3.06 | 3.43 | 1.78 |

Morphine & (+) Norketamine

| Male Rats 5-8 | | |
|---|---|---|
| Day 2 | Rats 5, 6 | 3 mg/kg Morphine & 3 mg/kg (+) Norketamine |
| Day 2 | Rats 7, 8 | 3 mg/kg Morphine & Saline |

TFL—Intensity 40%, idle activity 5%, cut-off 10 seconds
Solutions:
  1) Morphine—see p. 1
  2) (+) Norketamine—see p. 2

| Day 2 | Bwt. | |
|---|---|---|
| Rat 5 | 430 g | 0.430 ml Mor & 0.430 ml (+) Norketamine |
| Rat 6 | 415 g | 0.415 ml Mor & 0.415 ml (+) Norketamine |
| Rat 7 | 435 g | 0.435 ml Mor & 0.435 ml Saline |
| Rat 8 | 394 g | 0.394 ml Mor & 0.394 ml Saline |

| Rat | Baseline | Baseline | Inject Time | 15 min. | 30 min. | 60 min. | 120 min. |
|---|---|---|---|---|---|---|---|
| 5 | 1.55 | 1.63 | 10:35 | 3.54 | 4.92 | 6.20 | 2.96 |
| 6 | 1044 | 1.38 | | 2.97 | 5.70 | 10.0 | 7.62 |
| 7 | 116 | 1.10 | 10:36 | 2.25 | 2.46 | 3.83 | 2.60 |
| 8 | 1055 | 1.50 | | 1.56 | 1.97 | 2.08 | 2.24 |

What is claimed is:

1. A codrug of the following formula:

2. The codrug of claim 1, wherein the linker is selected from the group consisting of the following formulas:

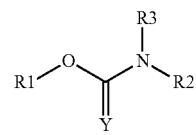

wherein Y is O or S; and R1-O is an opioid moiety and R2-N—R3 is a norketamine (R3=H) or ketamine (R3=CH$_3$) moiety

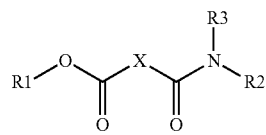

wherein X is nothing, O, S, NH, NR4 (R4=alkyl), (CH$_2$)$_x$ (where x=1-20, and the alkane moiety can be linear or branched), and wherein R2-N—R3 is a norketamine moiety (R3=H) or a ketamine moiety (R3=CH$_3$), and R1-O is an opioid moiety.

3. The codrug of claim 1, wherein the opioid is selected from the group consisting of dihydroetorphine, butorphanol, pentazocine, morphine, phenazocine, hydromorphone, codeine, 3-acetylmorphine, oxymorphone, methadone, propoxyphene, oxycodone, tramadol, hydrocodone, buprenorphine, levorphanol, dihydrocodeine, L-acetylmethadol, ethylmorphine, nalbuphine, etorphine, buprenorphine, normethadone, dihydromorphine, noroxycodone, normorphine, norlevorphanol, and pharmaceutically acceptable salts, metabolites, enantiomers, diastereiomers and isomers thereof.

4. The codrug of claim 2, wherein the norketamine is selected from the group consisting of S-norketamine, R-norketamine, and racemic norketamine, and pharmaceutically acceptable salts and metabolites thereof;

and wherein the ketamine is selected from the group consisting of S-ketamine, R-ketamine, and racemic ketamine, and pharmaceutically acceptable salts and metabolites thereof.

5. The codrug of claim 1 having the formula Ia:

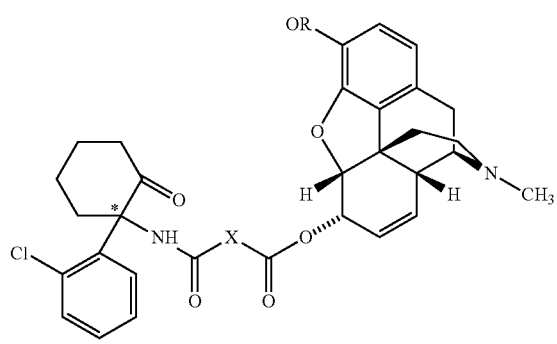

wherein X is a bond, $CH_2$, $(CH_2)_2$, or $(CH_2)_3$; R is H or $OCH_3$; and * represents racemic norketamine, S-norketamine, or R-norketamine; and analogs and stereoisomers thereof.

6. The codrug of claim 1 having the formula Ib:

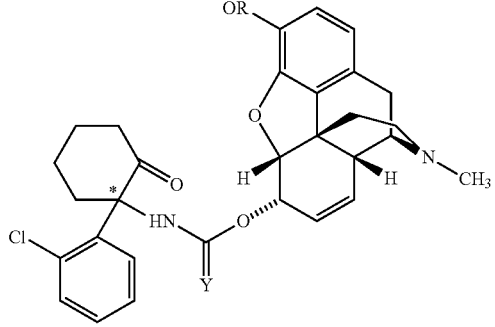

wherein Y is O, S, or $NR1$; R is H or $OCH_3$; R1 is alkyl; and * represents racemic norketamine, S-norketamine, or R-norketamine; and stereoisomers thereof.

7. The codrug of claim 1 having the formula II:

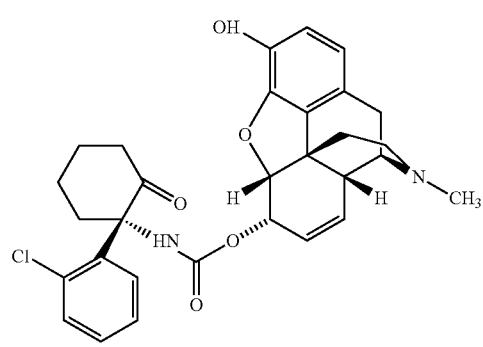

and stereoisomers thereof.

8. The codrug of claim 1 having the formula III:

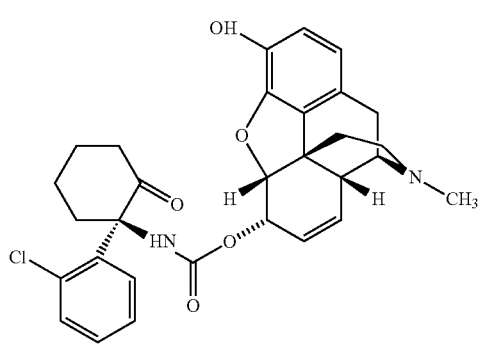

and stereoisomers thereof.

9. A codeine-racemic norketamine codrug having the formula:

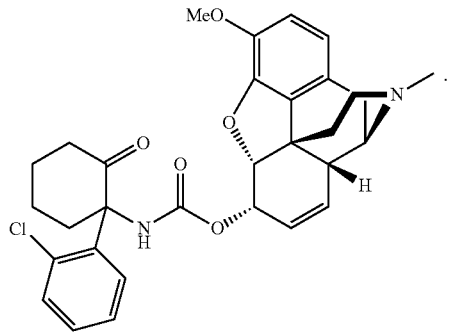

10. A codeine-racemic ketamine codrug comprising the formula:

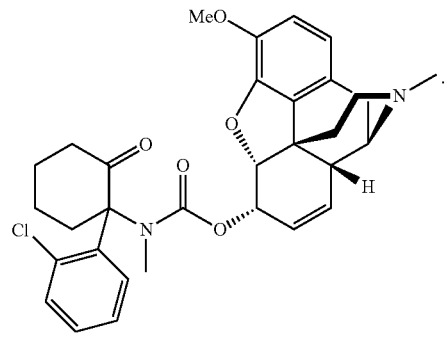

11. The codrug of claim 1, wherein the opioid moiety is morphine, and the ketamine moiety is S-ketamine, and wherein the linker is a carbamate.

12. The codrug of claim 1, wherein the opioid moiety is 3-acetylmorphine, and the ketamine moiety is S-ketamine, and wherein the linker is a carbamate.

13. The codrug of claim 1, wherein the opioid moiety is codeine, and the ketamine moiety is S-ketamine, and wherein the linker is a carbamate.

14. The codrug of claim 1, wherein the opioid moiety is oxycodone and the ketamine moiety is S-ketamine, and wherein the linker is a carbamate.

15. The codrug of claim 1, wherein the opioid moiety is oxymorphone, and the ketamine moiety is S-ketamine, and wherein the linker is a carbamate.

16. The codrug of claim 1, wherein the opioid moiety is hydromorphone, and the ketamine moiety is S-ketamine, and wherein the linker is a carbamate.

17. The codrug of claim 1, wherein the opioid moiety is butorphanol, and the ketamine moiety is S-ketamine, and wherein the linker is a carbamate.

18. The codrug of claim 1, wherein the opioid moiety is bupernorphine, and the ketamine moiety is S-ketamine, and wherein the linker is a carbamate.

19. The codrug of claim 1, wherein the opioid moiety is tramadol, and the ketamine moiety is S-ketamine, and wherein the linker is a carbamate.

20. The codrug of claim 1, wherein the opioid moiety is levorphanol, and the ketamine moiety is S-ketamine, and wherein the linker is a carbamate.

21. The codrug of claim 1, wherein the opioid moiety is morphine, and the norketamine moiety is S-norketamine, and wherein the linker is a carbamate.

22. The codrug of claim 1, wherein the opioid moiety is 3-acetylmorphine, and the norketamine moiety is S-norketamine, and wherein the linker is a carbamate.

23. The codrug of claim 1, wherein the opioid moiety is codeine, and the norketamine moiety is S-norketamine, and wherein the linker is a carbamate.

24. The codrug of claim 1, wherein the opioid moiety is oxycodone, and the norketamine moiety is S-norketamine, and wherein the linker is a carbamate.

25. The codrug of claim 1, wherein the opioid moiety is oxymorphone, and the norketamine moiety is S-norketamine, and wherein the linker is a carbamate.

26. The codrug of claim 1, wherein the opioid moiety is hydromorphone, and the norketamine moiety is S-norketamine, and wherein the linker is a carbamate.

27. The codrug of claim 1, wherein the opioid moiety is butorphanol, and the norketamine moiety is S-norketamine, and wherein the linker is a carbamate.

28. The codrug of claim 1, wherein the opioid moiety is bupernorphine, and the norketamine moiety is S-norketamine, and wherein the linker is a carbamate.

29. The codrug of claim 1, wherein the opioid moiety is tramadol, and the norketamine moiety is S-norketamine, and wherein the linker is a carbamate.

30. The codrug of claim 1, wherein the opioid moiety is levorphanol, and the norketamine moiety is S-norketamine, and wherein the linker is a carbamate.

31. A pharmaceutical composition comprising an analgesically effective amount of a compound selected from the group consisting of:

the compound of formula Ia:

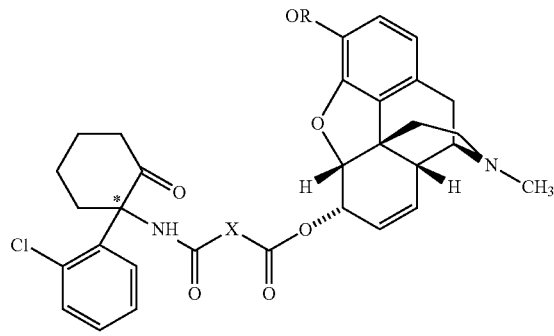

Ia wherein X is a bond, $CH_2$, $(CH_2)_2$, or $(CH_2)_3$; R is H or $OCH_3$; and * represents racemic norketamine, S-norketamine, or R-norketamine;

the compound of the formula Ib:

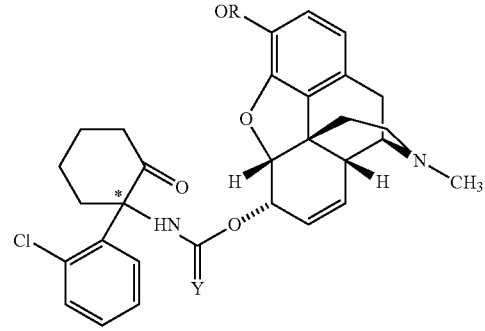

Ib wherein Y is O, S, or NR1; R is H or $OCH_3$; R1 is alkyl, and represents racemic norketamine, S-norketamine, or R-norketamine;

the compound of the formula II:

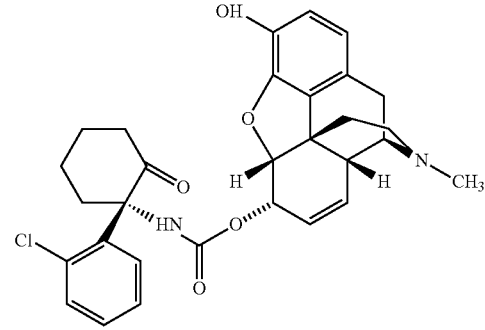

II and the compound of the formula III:

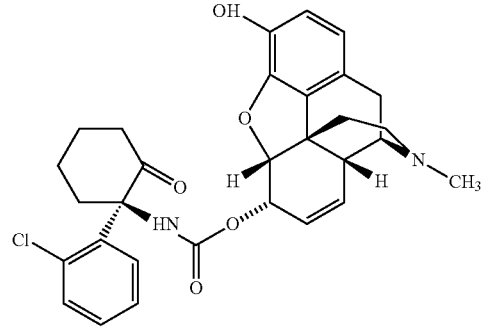

III and at least one pharmaceutically acceptable excipient.

32. The pharmaceutical composition of claim 31, wherein the compound is a compound of formula Ia and R is methyl.

33. The pharmaceutical composition of claim 31, wherein the compound is a compound of formula Ia and R is acetyl.

34. The pharmaceutical composition of claim 31, wherein the compound is a compound of formula Ia or Ib; and wherein X is a bond.

35. A pharmaceutical composition comprising the compound of claim 9, and at least one pharmaceutically acceptable excipient.

36. A pharmaceutical composition comprising the compound of claim 10 and at least one pharmaceutically acceptable excipient.

37. The pharmaceutical composition of claim 11, wherein the formulation is suitable for a route of administration selected from the group consisting of oral, sublingual, oral inhalation, nasal inhalation, sublingual, rectal, vaginal, urethral, intravenous, intra-arterial, intradermal, intramuscular, subcutaneous, transdermal, mucosal and buccal.

38. The pharmaceutical composition of claim 11, wherein the release of a codrug is substantially controlled over an extended period of time of about 4 hours to about 96 hours.

39. The pharmaceutical composition of claim 38, wherein the release of the codrug is substantially controlled for about 6-12 hours.

40. The pharmaceutical composition of claim 38, wherein the release of the codrug is substantially controlled for about 12-24 hours.

41. A method of synthesis of a codrug comprising a linker, an opioid and a ketamine or a norketamine, said method comprising:
  a) covalently bonding a first attachment point of the linker to the opioid;
  b) covalently bonding a second attachment point of the linker to the ketamine or norketamine; and
  c) recovering the codrug,
  wherein the norketamine is selected from the group consisting of S-norketamine, R-norketamine, and racemic norketamine; and
  wherein the ketamine is selected from the group consisting of S-ketamine, R-ketamine, and racemic ketamine.

42. The method of claim 41, further comprising:
  a) reacting para-nitrophenyl chloroformate with an opiate (opioid) (R1) containing a hydroxy group in the presence of triethyl amine and dry chloroform;
  b) cooling the solution;
  c) recovering the resulting 6-O-para-nitrophenoxycarbonate ester of an opiate drug;
  d) reacting the 6-O-para-nitrophenoxycarbonate ester of an opiate drug with a norketamine (R2); and
  e) recovering the ketamine-opioid or norketamine-opioid codrug.

43. The method of claim 41, wherein step b) is reacted in the presence of dry THF and triethyl amine.

44. The method of claim 41, wherein step b) occurs under cooled conditions and in a nitrogen atmosphere.

45. A method of treatment comprising:
  joining an opioid together with a ketamine or a norketamine using a linker to form a cleavable codrug; and
  administering an analgesically effective amount of the codrug to a human patient in need thereof,
  wherein the norketamine is selected from the group consisting of S-norketamine, R-norketamine, and racemic norketamine; and wherein the ketamine is selected from the group consisting of S-ketamine, R-ketamine, and racemic ketamine.

46. The method of claim 45, wherein the codrug substantially remains intact until it reaches the site of action of at least the opioid or the ketamine or norketamine.

47. The method of claim 45, wherein the codrug is more lipophilic than the opioid molecule.

* * * * *